United States Patent [19]

Shiozawa et al.

[11] Patent Number: 5,578,322

[45] Date of Patent: Nov. 26, 1996

[54] QUICK RELEASE COATED PREPARATION

[75] Inventors: Hiroyoshi Shiozawa; Hiroya Sugao; Shigeru Yamazaki, all of Fujieda; Katsuhiko Yano, Yaizu, all of Japan

[73] Assignee: Yamanouchi Pharmaceutical Co., Ltd., Tokyo, Japan

[21] Appl. No.: 458,793

[22] Filed: Jun. 2, 1995

Related U.S. Application Data

[63] Continuation of Ser. No. 70,324, filed as PCT/JP91/01594 filed Nov. 20, 1991, abandoned.

[30] Foreign Application Priority Data

Nov. 30, 1990 [JP] Japan .................................. 2-336057

[51] Int. Cl.$^6$ .............................. A61K 9/16; A61K 9/50
[52] U.S. Cl. .......................... 424/490; 424/488; 424/489
[58] Field of Search .................................. 424/489, 490, 424/488

[56] References Cited

U.S. PATENT DOCUMENTS

| | | | |
|---|---|---|---|
| 4,080,445 | 3/1978 | Lin | 424/227 |
| 5,000,965 | 3/1991 | Killeem | 426/5 |
| 5,057,319 | 10/1991 | Gottwald | 424/441 |
| 5,260,074 | 11/1993 | Sipos | 424/497 |

OTHER PUBLICATIONS

JP61238336 Fushiya Yoshihiko Preparation of Coated Material Having Gradual Release Property Oct. 23, 1986.

*Primary Examiner*—Thurman K. Page
*Assistant Examiner*—William E. Benston, Jr.
*Attorney, Agent, or Firm*—Burgess, Ryan and Wayne

[57] ABSTRACT

A coated preparation prepared by coating drug particles having a disagreeable taste with a mixture comprising a hydrophobic substance with a melting point of 45° to 90° C. and a surfactant with a lower melting point and heat treating the coating layer at a temperature ranging from around the melting point of the surfactant up to the melting point of the hydrophobic substance to modify the nature of the coating layer. This preparation can release the drug quickly which sufficiently suppressing the disagreeable taste.

18 Claims, 6 Drawing Sheets

55°C 12hr (x5000)

55°C 12hr (x5000)

55°C 3hr (x5000)

BEFORE AGING (x5000)

QUICK RELEASE COATED PREPARATION

This application is a continuation of application Ser. No. 08/070,324, filed as PCT/JP91/01594 Nov. 20, 1991, now abandoned.

TECHNICAL FIELD

This invention relates to a quick release coated preparation in which disagreeable taste is suppressed, and to a process for the production of the preparation.

BACKGROUND ART

Since a pharmaceutical preparation containing a drug having disagreeable taste, such as a bitter taste, generates the disagreeable taste when orally administered such a preparation is administered, in the dosage form of sugar-coated tablets, film-coated tablets, capsules or the like. On the other hand, because of a great demand for granular compositions which are convenient for preparation of pharmaceuticals, such as powders, fine granules, granules and the like, attempts have been made to suppress bitter tastes in these compositions. A typical example of such attempts may be a process for the production of a powder composition or the like in which a drug is dispersed in a melted waxy solid material having a melting point of from 40° to 100° C., the resulting mixture is solidified by jetting it from an exhaust nozzle or cooling it as it is, and then the solidified product is pulverized. However, since the property of drug release is not taken into consideration, the composition obtained by such a process cannot release the drug sufficiently in the digestive organs in spite of its excellent masking effect, thus decreasing bioavailability of the drug.

Such a problem may be resolved by blending a water soluble substance such as polyethylene glycol or a sucrose fatty acid ester having high HLB, but there is another problem that such a water soluble substance cannot be mixed uniformly with a waxy solid material in a melted state. Also, blending of water soluble excipients such as lactose, mannitol and the like is hardly effective in resolving the problem described above.

JP-A-54-95719 (the term "JP-A" as used herein means an "unexamined published Japanese patent application") discloses that fine granules obtained by melting a composition consisting of hardened oil, macrogol, and optionally a surfactant, suspending tiaramide hydrochloride as a principal bitter drug in the melted composition and then spray-solidifying the resulting suspension can suppress the bitter taste without reducing releasing of the principal agent. However, releasing ratio of the drug from the fine granules after 100 minutes is about 55%, and the releasing of the orally administered principal drug in the stomach is not satisfactory.

DISCLOSURE OF THE INVENTION

Under the aforementioned circumstances, the inventors of the present invention have conducted intensive studies and, as the result, have succeeded in developing a pharmaceutical preparation having bitter taste-suppressing effect and excellent drug releasing property.

Thus, the present invention provides a quick release coated preparation in which a disagreeable taste is suppressed, which is prepared by coating drug particles having a disagreeable taste with a mixture comprising a hydrophobic substance having a melting point of from 45° to 90° C. and a surfactant having a melting point of from 40° to 85° C., which is lower than that of the hydrophobic substance, wherein the surfactant in the coating layer is present in a redistributed state. The present invention also provides a process for the production of the preparation.

BEST MODE FOR CARRYING OUT THE INVENTION

Figure 1:
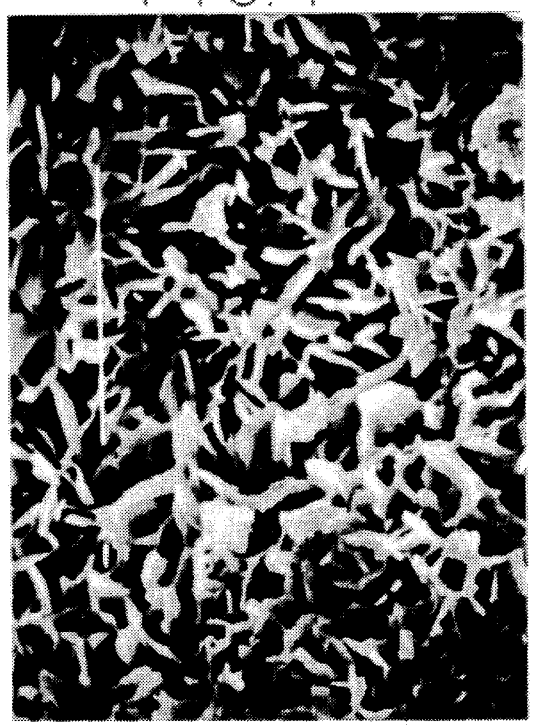
FIG. 1 is a microphotograph showing the surface of coated particles after 12 hours of aging of a 120% coat granulation product at 55° C. described in Example 1.

The following describes the present invention in detail.

The object of the present invention is to suppress disagreeable tastes of drugs having disagreeable tastes such as a bitter taste and the like. Examples of such drugs include berberine chloride, digitoxin, sulpyrine, ethylefrine hydrochloride, diltiazem hydrochloride, propranolol hydrochloride, chloramphenicol, aminophylline, erythromycin, phenobarbital, calcium pantothenate, indeloxazine hydrochloride, aminoguanidine hydrochloride and the like.

When these drugs are coated by means of spraying, the amount of a coating material required for the suppression of disagreeable tastes depends largely on the particle size distribution of the drug material, and fine powder especially having a mesh size of 325 or less suspends in a fluidized bed and a portion of the powder is not coated in some cases.

Accordingly, it is preferable to adjust particle size distribution of the drug material in advance in accordance with the following treatment. That is, fine powder of a drug material screened by force through a vibrating screen (100 mesh, for example) is fluidized in a fluidized bed and granulation is conducted with spraying a solution of an antistatic agent for preventing static adhesion to the fluidized bed tube and bag filter and excess aggregation of the drug, and then bulky particles are removed by forced screening through another vibrating screen (80 mesh, for example).

The quick release coated preparation of the present invention is produced by coating by a suitable method such as a spraying coating method, a drug having a disagreeable taste with a mixture comprising a hydrophobic substance having a melting point of from 45° to 90° C. and a surfactant having a melting point of from 40° to 85° C., which is lower than that of the hydrophobic substance, followed by aging.

The following illustratively describes the production process. First, a drug is fluidized in a fluidized bed granulating machine and a coating solution of a hydrophobic substance and a surfactant is sprayed thereto from a spray gun arranged at a side of the granulating machine, thereby conducting coating of the drug.

Of the coating materials used in the above drug coating step, the hydrophobic substance having a melting point of from 45° to 90° C. has a function to suppress disagreeable taste of the drug inside the mouth and the surfactant having a melting point of from 40° to 85° C. has a function to release the drug quickly in the stomach and intestines.

Examples of the hydrophobic substance having a melting point of from 45° to 90° C. include: petroleum waxes such as paraffin, petrolatum, microcrystalline wax and the like; animal waxes such as yellow beeswax, white beeswax, wool wax and the like; plant waxes such as carnauba wax, Japan wax, cocoa butter wax, palm wax and the like; fats such as cacao butter and the like; hardened oils and higher saturated fatty acid triglycerides, such as of beef tallow, lard, soybean oil, castor oil, rapeseed oil and the like; higher fatty acids such as lauric acid, stearic acid and the like; and higher alcohols such as cetyl alcohol, stearyl alcohol and the like. A mixture of two or more of these substances may also be used.

Of these hydrophobic substances, preferred substances are those having a melting point of from 55° to 90° C. Examples of such substances include yellow beeswax (melting point: 60° to 67° C.); white beeswax (melting point: 60° to 67° C.); carnauba wax (melting point: 80° to 86° C.); stearic acid (melting point: 56° to 72° C.); hardened rapeseed oil (melting point: 69° C.); and hardened castor oil (melting point: 85 to 87° C.).

Examples of the surfactant having a melting point of from 40° to 85° C. include sorbitan fatty acid esters, sucrose fatty acid esters, higher fatty acid monoglycerides, polyoxyethylene glycols such as PEG-6000, PEG-20000 and the like, polyoxypropylene glycols, polyoxyethylenepolyoxypropylene glycols, sodium lauryl sulfate and the like. A mixture of two or more of these surfactants may also be used.

Of these surfactants, those which are soluble in organic solvents and have a melting point in the range of from 45° to 60° C. are preferable. Examples of such surfactants include stearic acid ester of sucrose (melting point: 52° to 53° C.); oleic acid ester of sucrose (melting point: 50° to 54° C.); sorbitan monostearate (melting point: 53° C.); glycerol monostearate (melting point: 58° C.); polyoxyethylene[160] oxypropylene[30] glycol (melting point: 50° C.); PEG-2000 (melting point: 50° to 53° C.); PEG-4000 (melting point: 53.5° to 57.5° C.); PEG-6000 (melting point: 60° to 63° C.); and PEG-20000 (melting point: 62° to 68° C.).

Since these surfactants also have a function to prevent precipitation of the hydrophobic substance in a high concentration coating solution, they can prevent blockage in a spray gun in the coating step of the spray coating method.

With regard to quantitative relationships among the drug and coating materials, the surfactant may be used in an amount of from 2 to 30% by weight, preferably from 5 to 20% by weight, based on the hydrophobic substance, and the coating materials may be used in an amount of from 0.1 to 2.0 times the weight of the drug, and preferably in an amount of 0.4 or more the weight of the drug when the changes under severe conditions with the elapse of time are taken into consideration.

The drug thus coated with the coating materials is then made into pharmaceutical formulating preparations, if required. In the pharmaceutical preparation formulating step, the coated drug is granulated into a proper particle size together with fluidizing agents, water soluble excipients such as D-mannitol, lactose and the like, aqueous solution of water soluble coating materials such as hydroxypropylcellulose, hydroxypropylmethylcellulose, poly(vinyl pyrrolidone) and the like, using a fluidized bed granulating machine, etc. The types of pharmaceutical preparation include solid preparations such as powders, fine granules, granules, dry syrups and the like. When powders are the intended pharmaceutical preparation, it is desirable to pass the preparation through a 32 mesh vibrating screen after the coating.

According to the process of the present invention, an aging step is to effect the aging of mainly the coating layer of the drug.

The term "aging" as used herein means a method to redistribute the surfactant in the coating layer, and any conditions can be employed as long as the redistribution can be achieved. Preferably, the redistribution may be conducted by keeping the surfactant in a melted or near-melted state for an appropriate period of time under such conditions that the hydrophobic substance does not melt. A hot air treatment, etc. are appropriate for the treatment.

The aging may be conducted at a temperature of not lower than 30° C. but lower than the melting point of the hydrophobic substance, though it depends on the melting point of the surfactant. When the aging temperature is low, a prolonged period of time is required to obtain a preferable quick release property. When the aging temperature is high, the quick release property can be obtained within a short period of time, but there is a fear of a bad influence of high temperature upon the drug if the drug has a low stability to heat and the aggregation of particles due to the melting of waxes may occur.

In consequence, the aging may be achieved more effectively by selecting a combination of a hydrophobic substance having a melting point of from 55° to 90° C. with a surfactant having a melting point of from 45° to 60° C. and carrying out the aging at a temperature which is around the melting point of the surfactant and lower than the melting point of the hydrophobic substance, preferably in the range of from 50° to 60° C. In addition, it is preferable to carry out the aging at a lower temperature with spending a longer time, when the drug has a low stability to heat.

The aging time may be at least 1 hour, preferably for a period of from 3 to 24 hours, which may be selected suitably depending on the aging temperature and the intended degree of the quick release.

Aging at lower temperature may be realized by carrying out the aging under a reduced pressure.

It is known that a hydrophobic substance, such as wax or the like, and a water soluble surfactant cannot be mixed uniformly even when they are mixed under the melted state. It is assumed that redistribution of surfactant in a coating layer occurs due to their mutual reaction with surrounding hydrophobic substances when the surfactant molecules in the coating layer becomes an unstable melted or near-melted state by the aging of the coating layer. As the results, the surfactant projects in scaly shapes on the surface of the coating layer in the redistributed state, thus forming a fine irregular structure (see the drawings attached).

Incidentally, the aging step may be carried out prior to the pharmaceutical preparation formulating step, provided that the formulating step does not involve a step of heating at a temperature exceeding the melting point of the hydrophobic substance, and the aging step may also be carried out after the pharmaceutical preparation formulating step.

The coated preparation of the present invention thus obtained through the aforementioned steps can fully suppress disagreeable tastes such as a bitter taste of a drug contained in the preparation in the mouth, and the drug is released quickly in the stomach and intestines due to the effect of the redistributed surfactant. In this instance, a preparation prepared by coating a drug with a surfactant-lacking coating material (only a hydrophobic substance) shows slower drug releasing rate with aging, which is contrary to the preparation of the present invention. Also, drug releasing property of a coated preparation prepared without employing the aging step changes with the elapse of time while that of the aging-treated coated preparation hardly changes.

The following Examples and Comparative Examples are provided to further illustrate the present invention.

EXAMPLE 1

Using a fluidized bed granulating machine (Uni-Glatt), 300 g of indeloxazine hydrochloride was fluidized and 600 g of methylene chloride solution containing 2.5% of polyoxyethylene[160]polyoxypropylene[30] glycol (melting point, 50° C.) (Pluronic F-68, Asahi Denka Kogyo K.K.) was sprayed thereto for adjusting particle size, thereby obtaining granule.

To the thus obtained granule was sprayed a methylene chloride solution containing 10% of hardened rapeseed oil (melting point: 69.2° C.) (Lubriwax 103, Freund Sangyo Co., Ltd.), 1.4% of polyoxyethylene[160]polyoxypropylene[30] glycol (melting point, 50° C.) (Pluronic F-68, Asahi Denka Kogyo K.K.) and 0.1% of a sucrose fatty acid ester (melting point: 51° C. as an initiation point, 58° C. as a peak point and 69° C. as a melting point by DSC) (Ryoto-Sugar Ester S-370, Mitsubishi Kasei Corp.), thereby obtaining a 120% coat granulation product. Particle size distribution of the product is shown below.

| Particle sizes (mesh) | Ratio (%) |
| --- | --- |
| 60–80 | 32.9 |
| 80–100 | 27.0 |
| 100–150 | 18.7 |
| 150–200 | 12.1 |
| 200–250 | 3.1 |
| 250–325 | 4.1 |
| 325– | 2.1 |

Figure 2:
FIG. 2 is a microphotograph showing the surface of coated particles after 3 hours of aging of the 120% coat granulation product at 55° C. described in Example 1.
Figure 3:
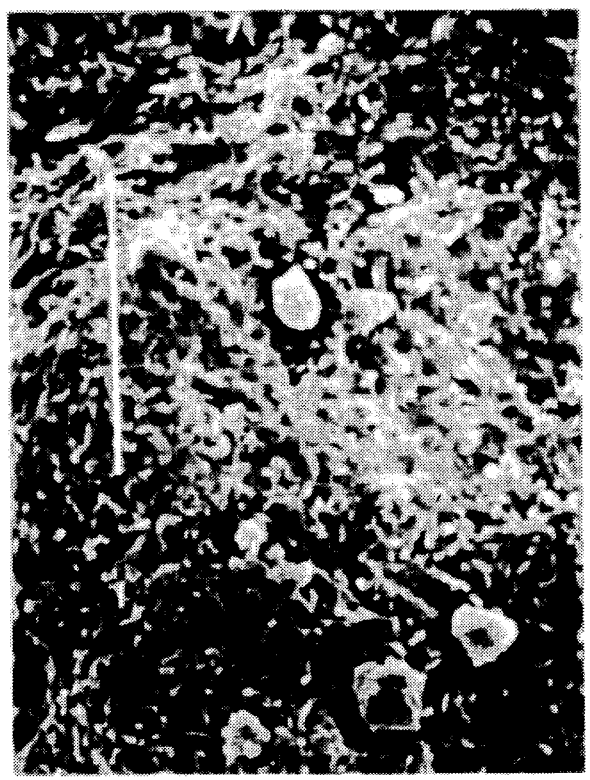
FIG. 3 is a microphotograph showing the surface of the 120% coat granulation product prior to aging described in Example 1.

The thus obtained 120% coat granulation product was subjected to aging, and redistribution of the surfactant was observed under a microscope. The results are shown in FIG. 1 (after 12 hours of aging by air-drying at 55° C.) and FIG. 2 (after 3 hours of aging under the same conditions). A microphotograph taken before the aging treatment is shown in FIG. 3 as a control.

EXAMPLE 2

To 22 g of the 120% coat granulation product obtained in Example 1 were added 0.22 g of a soft silicic acid anhydride (Adsolider 101, Freund Sangyo Co., Ltd.) as a fluidization agent and 100 g of D-mannitol and an appropriate amount of lactose as excipients, and granulation was conducted using 125 g of 10% aqueous solution of hydroxypropylcellulose to obtain 500 g in total of powder preparation. The thus obtained powder preparation was screened with a 32 mesh (500 μm) screen, and the screened preparation was subjected to 12 hours of aging by air-drying at 55° C.

Figure 4:
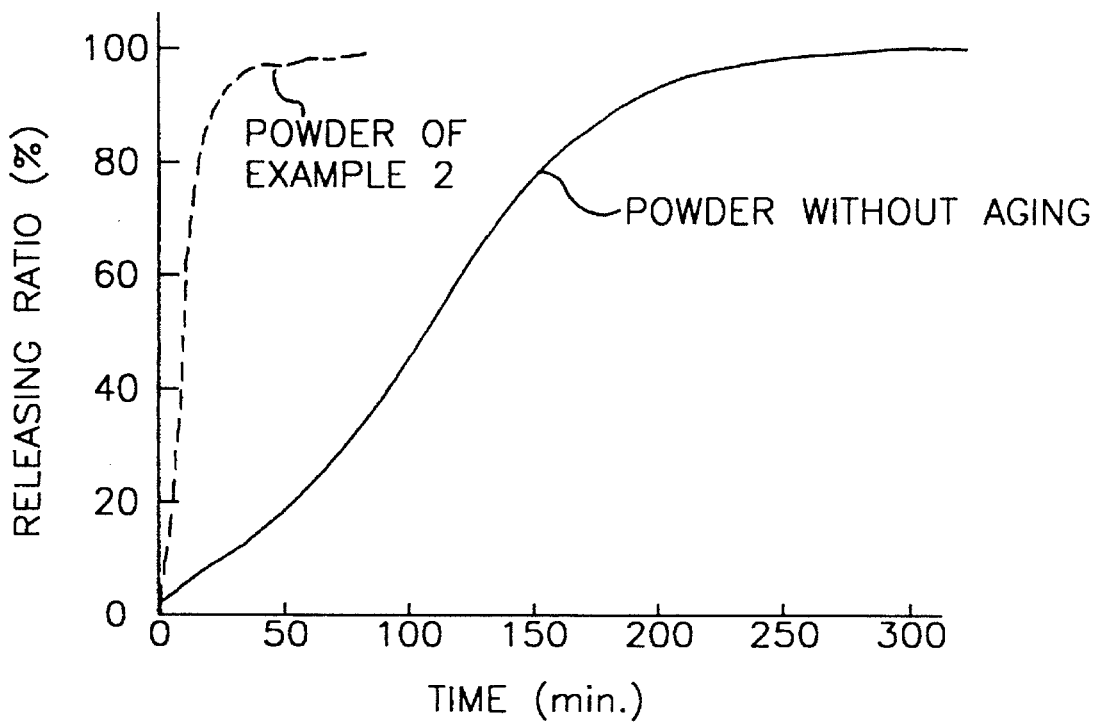
FIG. 4 is a graph showing a comparison of the releasing rate of a coated powder preparation obtained in Example 2 with that of a powder preparation with no aging treatment described in Example 2.
Figure 5:
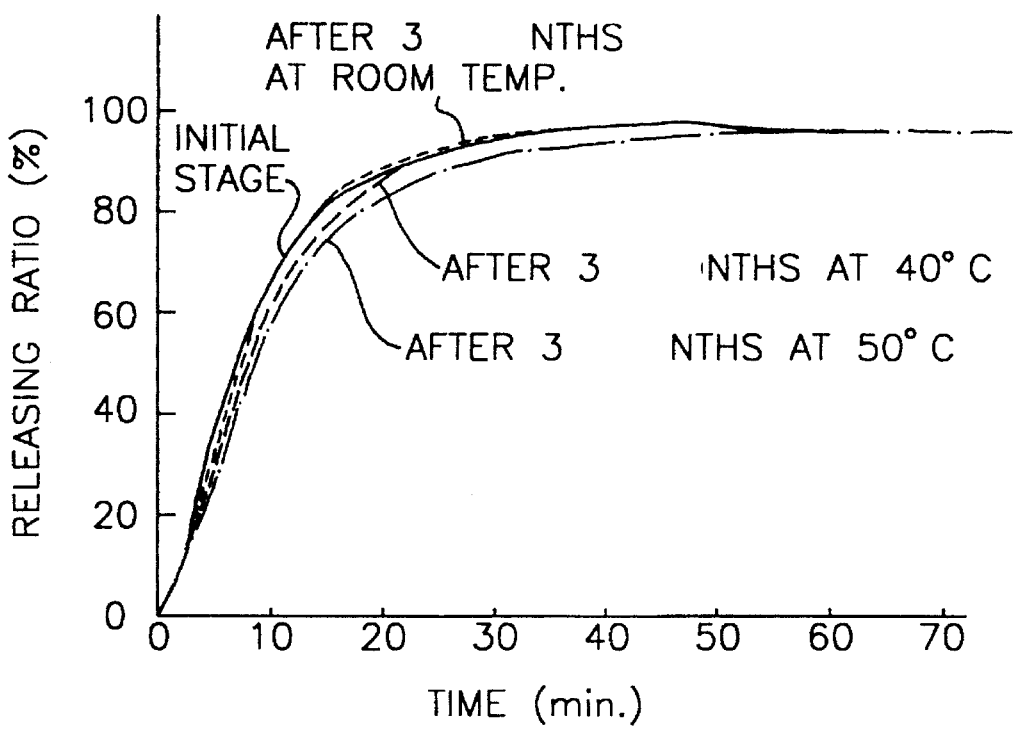
FIG. 5 is a graph showing changes in the releasing rate of the coated powder preparation of Example 2 with the passage of time. Data shown in this graph are those measured just after the preparation and after 3 months of storage at room temperature, 40° C. and 50° C.

A dissolution test was carried out at 50 rotations using 500 ml of purified water in accordance with the Dissolution Test 2 of The Pharmacopoeia of Japan. As shown in FIG. 4, great improvement of the releasing rate of the aging-treated powder preparation was confirmed. Bitter taste of the drug was suppressed for a period of about 60 seconds in the mouth even after storage under severe conditions (Note 1). In addition, as shown in FIG. 5, changes in the releasing rate with the elapse of time were hardly observed even after storage under severe conditions.

(Note 1)

Bitterness-suppressing effect was confirmed in the following manner.

(1) Threshold value test of astringent bitter taste of the drug

After washing out a panelist's mouth thoroughly with purified water, 10 ml of indeloxazine hydrochloride aqueous solution (100–300 μg/ml) is kept in the mouth. After about 10 seconds, contents in the mouth are spit out and the mouth is washed out, and the sensory evaluation of tastes is carried out based on the following 5 step judgement.

1: the same taste as water

2: different taste from water

3: a slightly bitter taste

4: a bitter taste

5: a strongly bitter taste

The results are shown in Table 1.

TABLE 1

| Sample | Results of Sensory Evaluation | | | | | | | | | | |
| | Panelists | | | | | | | | | | |
| (μg/ml) | A | B | C | D | E | F | G | H | I | J | Average |
| 100 | 1 | 1 | 1 | 1 | 1 | 2 | 1 | 2 | 1 | 3 | 1.3 |
| 150 | 2 | 2 | 1 | 1 | 2 | 2 | 1 | 2 | 1 | 2 | 1.6 |
| 200 | 2 | 2 | 3 | 2 | 3 | 3 | 2 | 3 | 2 | 2 | 2.4 |
| 250 | 3 | 4 | 3 | 2 | 3 | 3 | 2 | 3 | 2 | 2 | 2.7 |
| 300 | 3 | 5 | 4 | 3 | 2 | 4 | 2 | 4 | 4 | 2 | 3.3 |

As is evident from the above results of the sensory evaluation by the threshold test, a bitter taste is detectable generally at a drug concentration of 200 μg/ml in the case of indeloxazine hydrochloride.

(2) In vitro evaluation of astringent bitter taste of the drug (simplified dissolution)

A 5 ml capacity syringe is charged with the powder preparation of Example 2 (powder preparation after 12 hours of aging at 55° C.) in an amount equivalent to 10 mg of indeloxazine hydrochloride. 5 ml of purified water at 37° C. is added thereto, and the sample is mixed with purified water by repeating upside down motion of the syringe at a frequency of 10 times per 30 seconds. Thereafter, a Millipore filter (0.45 μm in pore size) is attached to the tip of the syringe to filter the contents. The resulting filtrate is diluted 10 times with purified water, and absorbance at 248 nm is measured after 60 seconds of the dilution step.

The results of the simplified dissolution test are shown in Table 2, which coincided with the results of an sensory test.

TABLE 2

Results of Simplified Dissolution Test

| Sample | Indeloxazine Hydrochloride Concentration (μg/ml) 60 Seconds |
|---|---|
| Example 2 (Just After Production) | 125.6 |
| (After 3 Months of Storage at Room Temp.) | 136.6 |
| (After 3 Months of Storage at 50° C.) | 138.5 |

Results of sensory test:

Each of the samples was not detectable 60 seconds after the dilution step, but was detected after about 120 seconds.

COMPARATIVE EXAMPLE 1

Figure 6:
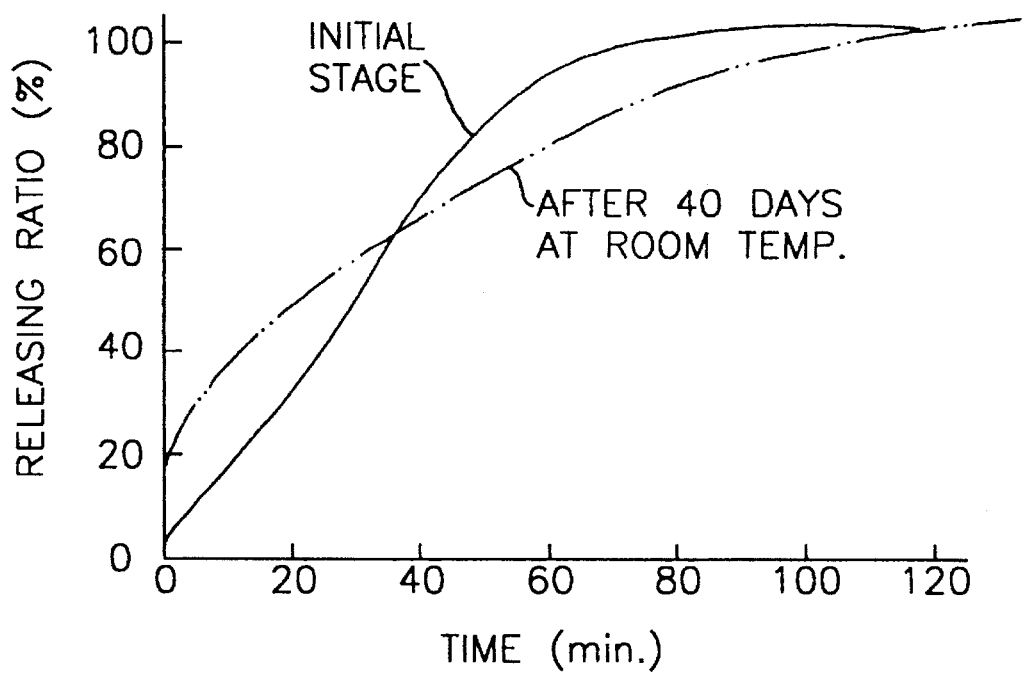
FIG. 6 is a graph showing changes in the releasing rate of a coated powder preparation of Comparative Example 1 with the passage of time, which were measured just after the preparation and after 40 days of storage at room temperature.

A powder preparation was prepared in the same manner as described in Example 2 except that the aging was not carried out. Changes in the releasing rate of this powder preparation with the elapse of time, which are measured at an early stage and after 40 days of storage at room temperature, are shown in FIG. 6. Bitter taste of the drug in the mouth was suppressed for about 60 seconds.

As is evident from the comparison of this drawing with FIG. 5, releasing rate of the powder preparation of Comparative Example 1 in which aging treatment was not carried out is slower than that of the aging-treated preparation of Example 2 and the releasing ratio of the former changes with the elapse of time.

COMPARATIVE EXAMPLE 2

A coat granulation product was prepared by repeating the process of Example 1, except that a methylene chloride solution containing 10% of hardened rapeseed oil (Lubriwax 103, Freund Sangyo Co., Ltd.) was used in the spraying instead of the three components containing methylene chloride solution used in Example 1, and the granulation product thus obtained was made into a powder preparation and subjected to aging in the same manner as described in Example 2. Bitter taste of the drug in the mouth was suppressed for a period of about 60 seconds.

Figure 7:
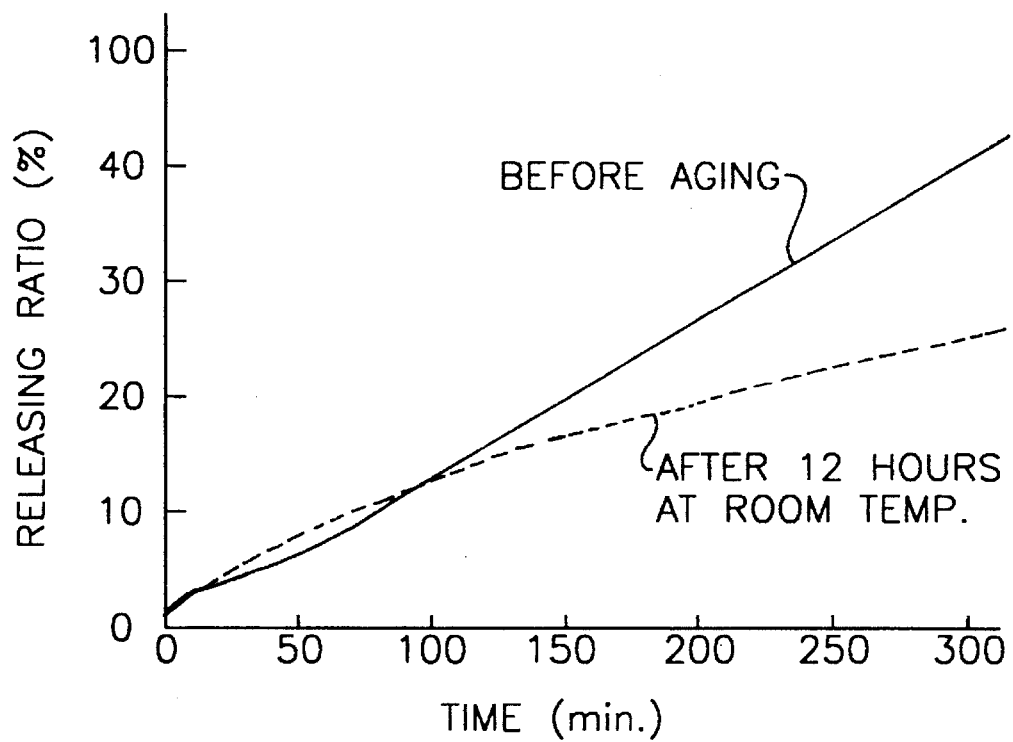
FIG. 7 is a graph showing releasing rates of a coated powder preparation of Comparative Example 2 measured before aging and after 12 hours of aging at 55° C.

As shown in FIG. 7, improvement of the drug-releasing rate by the aging treatment was not found at all in the powder preparation of Comparative Example 2 in which surfactant was not used.

EXAMPLE 3 a) A 125% coat granulation product was prepared by repeating the process of Example 1, except that a methylene chloride solution containing 10% of hardened rapeseed oil and 0.5% of a sucrose fatty acid ester was used in the spraying instead of the three components-containing methylene chloride solution used in Example 1. The granulation product thus obtained was made into a coated powder preparation in the same manner as described in Example 2.

b) In the same manner, a 150% coat granulation product was prepared using a methylene chloride solution containing 10% of hardened rapeseed oil and 1.0% of a sucrose fatty acid ester instead of the three components-containing methylene chloride solution. The thus obtained granulation product was made into a coated powder preparation in the same manner as in Example 2.

c) In the same manner, a 150% coat granulation product was prepared by spraying a methylene chloride solution containing 10% of hardened rapeseed oil and 2.0% of a sucrose fatty acid ester instead of the three components-containing methylene chloride solution. The thus obtained granulation product was made into a coated powder preparation in the same manner as described in Example 2.

Each of the thus prepared powder preparations fully suppressed bitter taste of the drug.

Dissolution test:

The time (minute) required to release a 75% portion of the total amount of the drug (T75% (min)) is measured with respect to each of the coated powder preparation obtained in this Example with no aging treatment (pre-aging) or after 12 hours of aging treatment at 55° C. (post-aging). The results are shown in the following Table 3.

TABLE 3

| Preparations Tested | T75% (min) | |
|---|---|---|
| Example | Pre-Aging | Post-Aging |
| 3-a | 106.3 | 26.6 |
| 3-b | 42.9 | 5.2 |
| 3-c | 13.1 | 2.5 |

As shown in Table 3, releasing rate of the drug from the coated powder preparation was greatly improved by the aging treatment in comparison with the case of no aging treatment. This means that the drug is quickly released in the stomach and intestines when the coated powder preparation of the present invention is administered, thus markedly improving effective availability of the drug.

EXAMPLE 4 a) A 150% coat granulation product was prepared by repeating the process of Example 1, except that a methylene chloride solution containing 10% of hardened rapeseed oil and 2.0% of polyoxyethylene[160]polyoxypropylene[30] glycol was used in the spraying instead of the three components-containing methylene chloride solution used in Example 1. The granulation product thus obtained was made into a coated powder preparation in the same manner as described in Example 2.

b) In the same manner, an 80% coat granulation product was prepared by spraying a methylene chloride solution containing 10% of hardened rapeseed oil and 1.5% of polyoxyethylene[160]polyoxypropylene[30] glycol instead of the three components-containing methylene chloride solution. The thus obtained granulation product was made into a powder preparation in the same manner as in Example 2 and then subjected to 3 days of aging by air-drying at 50° C.

Each of the thus prepared powder preparations fully suppressed bitter taste of the drug.

Dissolution test:

Each of the coated powder preparations thus obtained was subjected to the dissolution test in the same manner as described in Example 3. The results are shown in Table 4.

TABLE 4

| Preparations Tested | T75% (min) | |
|---|---|---|
| Example | Pre-Aging | Post-Aging |
| 4-a | 57.1 | 30.3 |
| 4-b | 34.7 | 8.8 |

EXAMPLE 5

Using a fluidized bed granulating machine (Uni-Glatt), 300 g of aminoguanidine hydrochloride (particle size: 125–500 μm) was fluidized and a methylene chloride solution containing 10% of hardened rapeseed oil, 1.4% of polyoxyethylene[160]polyoxypropylene[30] glycol and 0.1% of a sucrose fatty acid ester was sprayed thereto, thereby obtaining a 40% coat granulation product.

The thus obtained product was Subjected to 15 hours of aging by air-drying at 55° C.

Figure 8:
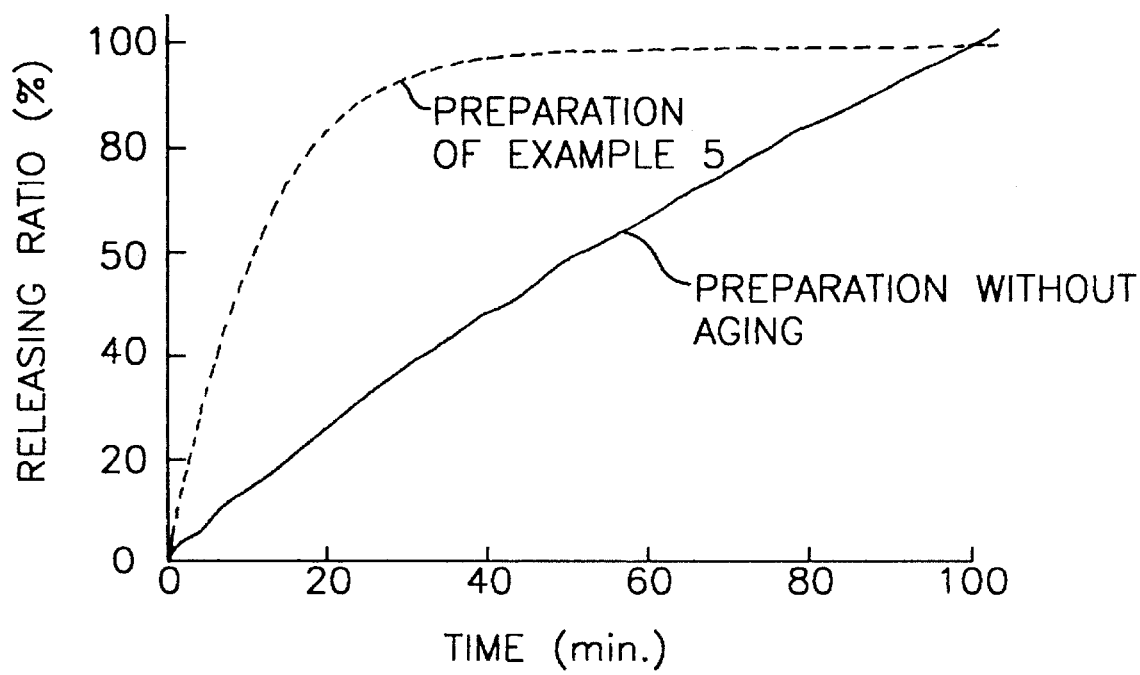
FIG. 8 is a graph showing a comparison of the releasing rate of a coated powder preparation obtained in Example 5 with that of a powder preparation with no aging treatment described in Example 5.

A dissolution test was carried out at 100 rotations using 500 ml of 0.1% Tween 80 aqueous solution in accordance with the Dissolution Test 2 of The Pharmacopoeia of Japan. As shown in FIG. 8., great improvement of the releasing rate of the aging-treated granulation product was confirmed. Bitter taste of the drug was suppressed for a period of about 60 seconds in the mouth both before and after the aging treatment.

EXAMPLE 6

Using a fluidized bed granulating machine (Uni-Glatt), 300 g of indeloxazine hydrochloride (particle size: 125–500 μm) was fluidized and a methylene chloride solution containing 10% of stearic acid (63 Stearin, Kawaken Fine Chemical), 1.4% of polyoxyethylene[160]polyoxypropylene[30] glycol and 0.1% of a sucrose fatty acid ester was sprayed thereto, thereby obtaining a 40% coat granulation product.

The thus obtained product was subjected to 15 hours of aging by air-drying at 55° C.

Figure 9:
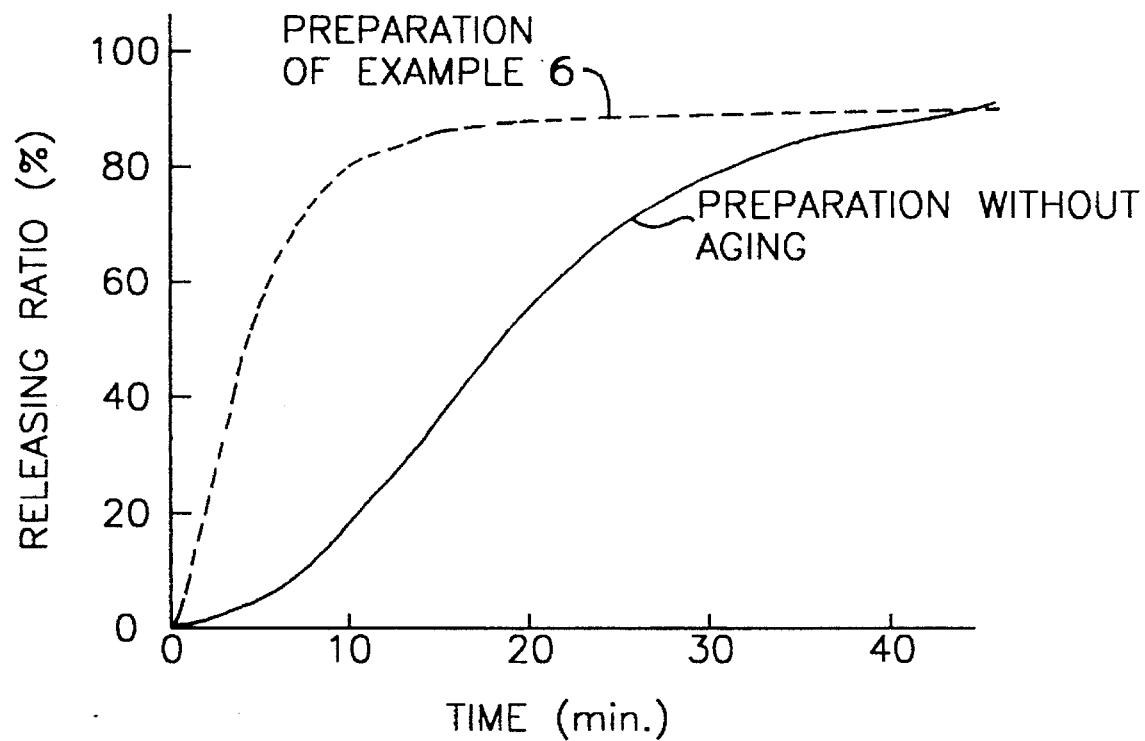
FIG. 9 is a graph showing a comparison of the releasing rate of a coated powder preparation obtained in Example 6 with that of a powder preparation with no aging treatment described in Example 6.

A dissolution test was carried out at 100 rotations using 500 ml of 0.1% Tween 80 aqueous solution in accordance with the Dissolution Test 2 of The Pharmacopoeia of Japan. As shown in FIG. 9, great improvement of the releasing rate of the aging-treated granulation product was confirmed. Bitter taste of the drug was suppressed for a period of about 60 seconds in the mouth both before and after the aging treatment.

EXAMPLE 7

A 120% coat granulation product was prepared in the same manner as described in Example 1.

To 22 g of the 120% coat granulation product thus prepared were added 0.22 g of a soft silicic acid anhydride as a fluidization agent, 150 g of D-mannitol as an excipient and appropriate amounts of sucrose and perfume, and granulation was conducted using 125 g of 10% hydroxypropylcellulose solution to obtain 500 g in total of dry syrup. The thus obtained dry syrup was subjected to 15 hours of aging by air-drying at 55° C.

When a dissolution test was carried out at 100 rotations using 500 ml of 0.1% Tween 80 aqueous solution in accordance with the Dissolution Test 2 of The Pharmacopoeia of Japan, great improvement of the releasing rate of the aging-treated dry syrup was found similar to the case of the powder preparation. When the dry syrup was dispersed in 5 ml of purified water and subjected to a sensory test, bitter taste of the drug was found to be suppressed even after 10 minutes of the dispersion.

EXAMPLE 8

The process of Example 1 was repeated by spraying the three components-containing methylene chloride solution, except that an 80% coat granulation product was obtained instead of the 120% coat granulation product. The thus obtained granulation product was treated in the same manner as described in Example 2 to make the product into a coated powder preparation. The coated power preparation was subsequently subjected to aging by air-drying under the following varied conditions.

a) 3 days at 50° C. (under a reduced pressure of 10 mmHg)

b) 12 hours at 55° C.

c) 12 hours at 60° C.

d) 17 hours at 52° C.

Figure 10:
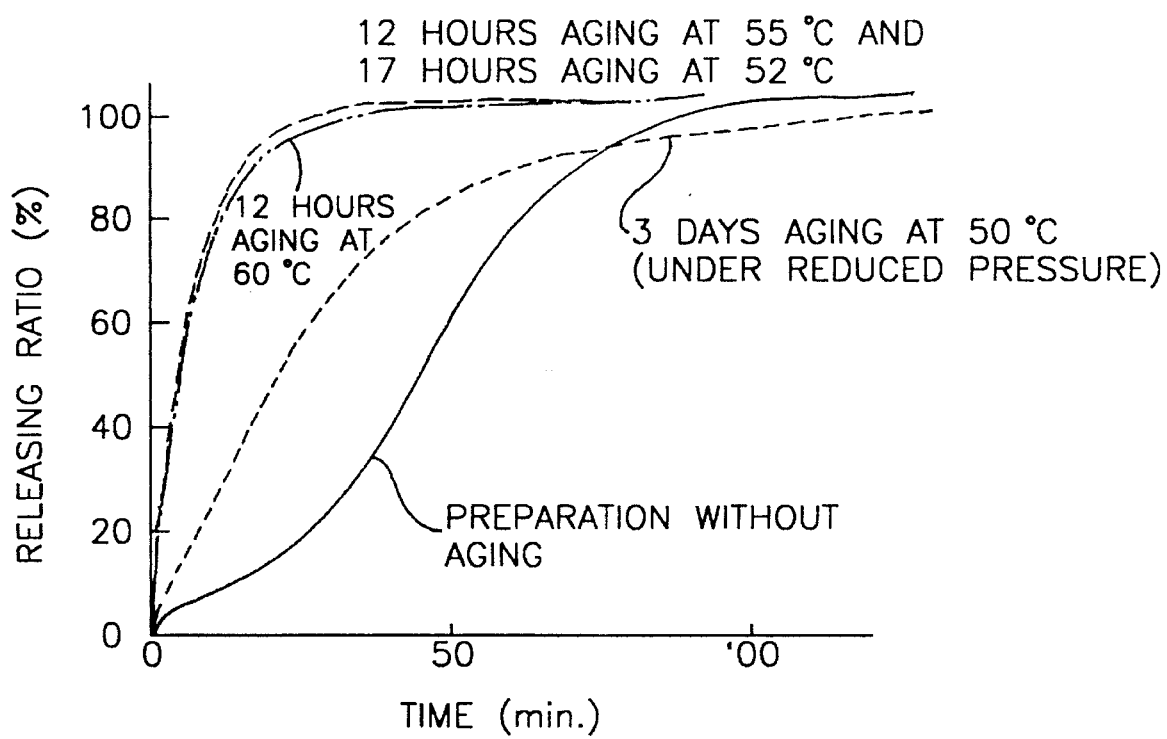
FIG. 10 is a graph showing a comparison of the releasing rate of a coated powder preparation obtained in Example 8 with that of a powder preparation with no aging treatment described in Example 8.

Dissolution test:

The T75% (min) value was measured with respect to each of the aged preparation. The results are shown in Table 5 and FIG. 10.

TABLE 5

| Preparations Tested Example | T75% (min) |
|---|---|
| 8-a | 35.5 |
| 8-b | 9.8 |
| 8-c | 10.1 |
| 8-d | 11.8 |
| Control (Before Aging) | 57.3 |

INDUSTRIAL APPLICABILITY

As has been described in detail in the foregoing, the coating layer of the coated preparation of the present invention, which comprises a hydrophobic substance and a surfactant, is heat-treated at a temperature around the melting point of the surfactant and lower than the melting point of the hydrophobic substance, thereby succeeding in modifying the property of the coating layer. By this modification, the coated preparation of the present invention can release the drug quickly while sufficiently suppressing disagreeable tastes of the drug. In the prior art coated preparations in which hydrophobic substances are used, sufficient suppression of disagreeable tastes causes delay in the dissolution and decrease in the bioavailability. Such problems involved in the prior art have been resolved by the present invention. The coated preparation of the present invention can be applied not only to tablets and powders but also to dry syrups.

We claim:

1. A quick release coated preparation in which a disagreeable drug taste is suppressed, which comprises drug particles having a disagreeable taste coated with a mixture comprising a hydrophobic substance having a melting point of from 45° to 90° C. and a surfactant having a melting point of from 40° to 85° C., which is lower than that of the hydrophobic substance, wherein the surfactant in the coating layer is present in a redistributed state.

2. The quick release coated preparation according to claim 1, wherein said preparation is obtained by heating at a temperature of not lower than 30° C. and lower than a melting point of the hydrophobic substance for a period of at least 1 hour.

3. The quick release coated preparation according to claim 2, wherein said hydrophobic substance is a higher fatty acid or a hardened oil having a melting point of from 55° to 90° C., and wherein said surfactant is a surfactant which has a melting point of from 45° to 60° C. and is soluble in organic solvent.

4. A process for producing a quick release coated preparation in which a disagreeable drug taste is suppressed, which comprises coating drug particles with a mixture comprising a hydrophobic substance having a melting point of from 45° to 90° C. and a surfactant having a melting point of from 40° to 85° C., which is lower than that of the hydrophobic substance, and carrying out aging of the coating layer of the drug particles at a temperature of not lower than 30° C. and lower than a melting point of the hydrophobic substance.

5. The process according to claim 4, wherein the aging is carried out for at least 3 hours at a temperature at about the melting point of the surfactant and lower than a melting point of the hydrophobic substance.

6. The quick release coated preparation of claim 1 wherein the hydrophobic substance is yellow beeswax.

7. The quick release coated composition of claim 1 where the hydrophobic substance is stearic acid.

8. The quick release coated preparation of claim 1 wherein the hydrophobic substance is hardened rapeseed.

9. The quick release coated composition of claim 1 wherein the hydrophobic substance is hardened castor.

10. The quick release coated composition of claim 1 wherein the surfactant is polyoxyethylene [160]-oxypropylene [30] glycol.

11. The quick release coated composition of claim 1 wherein the surfactant is the stearic acid ester of sucrose.

12. The quick release coated composition of claim 1 wherein the surfactant is the oleic acid ester of sucrose.

13. The quick release coated composition of claim 1 wherein the surfactant is sorbitan monostearate.

14. The quick release coated composition of claim 1 wherein the drug is indeloxazine hydrochloride.

15. The quick release coated composition of claim 1 wherein the drug is aminoguanidine hydrochloride.

16. The quick release coated composition of claim 1 wherein the drug is digitoxin.

17. The quick release coated composition of claim 1 wherein the drug is propranolol hydrochloride.

18. A process for administering a drug to a patient wherein the disagreeable taste of the drug is suppressed which comprises coating the particles of the drug having a disagreeable taste with a mixture comprising a hydrophobic substance having a melting point of from 45° to 90° C. and a surfactant having a melting point of from 40° to 85° C., which is lower than that of the hydrophobic substance, and aging the coating layer of said drug particles at a temperature not lower than 30° C. and lower than a melting point of the hydrophobic substance, and thereafter administering the resulting drug product to the patient.

* * * * *